United States Patent [19]

Silverman et al.

[11] Patent Number: 4,571,682

[45] Date of Patent: Feb. 18, 1986

[54] SYSTEM AND METHOD FOR SKILL ENHANCEMENT AND BEHAVIOR MODIFICATION

[75] Inventors: Gordon Silverman; Joseph Brudny, both of New York, N.Y.

[73] Assignee: Computerized Sports Equipment, Inc., New York, N.Y.

[21] Appl. No.: 525,165

[22] Filed: Aug. 22, 1983

[51] Int. Cl.⁴ ..................... G06F 15/42; G06F 15/16
[52] U.S. Cl. .................................. 364/413; 364/415; 364/551; 272/129; 272/DIG. 6
[58] Field of Search ............... 364/413, 415, 550–552; 272/116–117, 129, DIG. 6; 73/379; 340/384 E, 384 R

[56] References Cited

U.S. PATENT DOCUMENTS

| | | | |
|---|---|---|---|
| 3,087,487 | 4/1963 | Clynes | 364/413 X |
| 3,717,857 | 2/1973 | Evans | 340/177 R |
| 3,905,355 | 9/1975 | Brudny | 128/2.1 M |
| 3,929,335 | 12/1975 | Malick | 272/129 X |
| 3,972,320 | 8/1976 | Kalman | 364/415 X |
| 4,110,918 | 9/1978 | James et al. | 35/22 R |
| 4,136,684 | 1/1979 | Scattergood et al. | 128/2.1 M |
| 4,137,566 | 1/1979 | Haas et al. | 364/410 |
| 4,163,941 | 8/1979 | Linn, Jr. | 324/178 |
| 4,170,225 | 10/1979 | Criglar et al. | 128/733 |
| 4,197,854 | 4/1980 | Kåsa | 364/415 X |
| 4,216,462 | 8/1980 | McGrath et al. | 364/415 X |
| 4,235,437 | 11/1980 | Ruis et al. | 272/129 X |
| 4,244,021 | 1/1981 | Chiles, III | 364/413 |
| 4,250,890 | 2/1981 | Jones et al. | 128/728 |
| 4,304,406 | 12/1981 | Cromarty | 273/186 R |
| 4,337,049 | 6/1982 | Connelly | 434/247 |
| 4,356,475 | 10/1982 | Neumann et al. | 364/415 X |
| 4,375,674 | 3/1983 | Thornton | 364/522 X |

FOREIGN PATENT DOCUMENTS

| | | | |
|---|---|---|---|
| 2822343 | 11/1979 | Fed. Rep. of Germany | 272/129 |
| WO82/02668 | 8/1982 | PCT Int'l Appl. | 272/129 |

Primary Examiner—Gary V. Harkcom

[57] ABSTRACT

Structural systems and method are employed including a multiplicity of computers to control the acquisition and enhancement of skilled performance or behavior. Preprocessing computers (8 and 24) each accept signals from any corresponding one of a variety of physiological or other signal transducers either in close proximity to the computer or transmitted to the computer via a telemetering system. The preprocessing computer calculates a number of different measures of this signal and makes the results known to one or more other computers. These other or auxiliary computers control presentation of a display of the data for a human observer, and perform additional calculations which determine if the processed data is within a predetermined range. This range may be a function of time and/or other variables. A measure of the error between the allowed range and the processed data is computed within these auxiliary computers. These results may be used to alter the display. They are also returned to the preprocessing computer where they may alter the preprocessing calculations. Alteration of the display and the preprocessing calculations are adapted to improve skilled performance and behavior without the intervention of a human operator other than the user.

14 Claims, 5 Drawing Figures

Fig. 2.
Computer Block Diagram

Fig. 4A.
Flow Diagram

SYSTEM AND METHOD FOR SKILL ENHANCEMENT AND BEHAVIOR MODIFICATION

BACKGROUND OF INVENTION

In the past, the introduction of signals which are electrical analogs of physiological signals into a computer or display has been used primarily for one of three purposes.

(1) Acquisition of data concerning physiological and/or behavioral responses, possibly to some external stimuli.

(2) Physical rehabilitation of human subjects who have lost motor control as a result of some injury or insult to the central nervous system or other parts of the body.

(3) Psychological treatment of altered behavior due to heightened anxiety and stress.

Computer application in the fields of science and medicine led to tremendous advances in these areas. However, these advances have not yet been adapted or reflected in the methodology of instructing people to improve their fitness or performance in sports. In man, the effectors of behavior are primarily the muscles. Their skillful use, in terms of appropriate spatio-temporal and coordinated activity requires learning that leads to eventual patterning or automatic responses. Acquisition of skill is accomplished through very many successful, and properly identified to be successful, repetitive trials. Skill enhancement maximizes the role of the effectors of behavior (muscles) and adds to well-being and fitness.

PRIOR ART

There are many skill enhancement machines and systems designed to improve athletic and/or other performance or behavior in healthy, normal individuals. Such presently available systems, however, suffer from a number of limitations. Most do not employ computers for learning, offering only various types of mechanical resistance to cause muscular contractions. The inherent inability of human beings to finely quantify effort without on-line, real-time augmented feedback makes such contractions either excessive and too widely spread or too inadequate to be effective. The ones that employ computers, use "off-line" techniques for the improvement of skilled behavior. This means that skill improvement occurs as a result of a sequence of operations (knowledge of results). Thus and first, performance or behavioral data is acquired from a subject and stored in a computer. Next, the data is reviewed (after the activity has been completed) and adjustments in the performance are determined. This process is repeated until some behavioral goal is achieved. The delay in the feedback of behavior has been demonstrated to be ineffective for learning or improving skilled performance.

Other machines display a measure of the subject's performance but these may not provide behavioral goals. Thus, a human operator is needed to provide for the target goals. Where the machine includes behavioral goals as part of the display, these goals are often fixed. As a consequence, the machine by itself is incapable of "adaptive" or dynamic operation. This limits the rate and level of peformance which can be achieved.

Still other machines do employ some dynamic, adaptive operation. However, these rely on behavioral measures of human performance such as position, and not on underlying physiological signal sources. A subject training signal is provided only when performance falls outside an allowed error range. The subject is unaware of the instantaneous and continuous value of his or her error.

A primary limitation of these machines is related to their organization or architecture. Most machines include a single computer or processor which must carry out all operations associated with the acquisition of data, display of results, and calculation of performance goals. Such machines cannot perform all instructions associated with these calculations within a specified time (real time). As a consequence, the subject cannot obtain an accurate representation of his or her behavior. Results are only made available after a considerable delay in time. This limits improvement of skill acquisition.

This criticism of prior art includes typical structures, systems and methods reflected in the following U.S. patents:

J. W. Evans; 3,717,857; Feb. 20, 1973
J. Brudny; 3,905,355; Sept. 16, 1975
J. W. James et al.; 4,110,918; Sept. 5, 1978
M. G. Scattergood et al.; 4,136,684; Jan. 3, 1979
S. L. Haas et al.; 4,137,566; Jan. 30, 1979
R. N. Linn; 4,163,941; Aug. 7, 1979
J. J. Crigler et al.; 4,170,225; Oct. 9, 1979
W. C. Jones et al.; 4,250,890; Feb. 17, 1981
J. I. Cromarty; 4,304,406; Dec. 8, 1981
E. M. Connally; 4,337,049; June 29, 1982

Evans 3,717,857 discloses an athletic measurement system and apparatus in which a dedicated (fixed, and non-interchangeable) transducer provides definite information about flex and twist of a plate affixed to an arm or within an arm or club. Means such as a cathode ray tube or oscillograph, are included for display of a swing initiated by a human being. However, this device is limited to measurement of a single behavioral activity and provides only a fixed computation with regard to the data being generated by the human being.

Brudny 3,905,355 describes an apparatus for obtaining and displaying muscle activity at a multiplicity of points on the human body with structure to display, in a multiplicity of forms, a single measure of such activity, and includes an adjustable reference means which can be used by a human being to compare his own responses against this adjustable reference. This system includes a single computer with a single program of operations whose function is to calculate one measure of performance of EMG activity. The computer provides a single result which is used by the display alone and cannot integrate or coordinate the independent actions of other computers which can carry out distinct operations.

James et al. 4,110,918 includes portable, self-contained modular units which may be used for biofeedback training. A central processing unit can be adapted to receive inputs in a simultaneous manner from multiple portable units and provides additional refined conditioning of the signals from the portable units. However, the central processor cannot initiate, synchronize, control, nor vary the preprocessing calculations and the results generated by the portable units.

Scattergood et al. 4,136,684 provides an example of a biofeedback system which can operate over a wide dynamic range extending from one microvolt of signal to signal levels in excess of one millivolt. However, this system is limited to a single calculation and has no provision for interchangeable transducers in order to permit its use with other physiological signals and applications such as those underlying EKG behaviors or temperature responses for use in reduction of stress.

Haas et al. 4,137,566 presents an example of a system intended for use where "knowledge of results" is important. An apparatus and method for analyzing a golf swing and displaying results is shown. This apparatus is limited to processing of positional information and provides no means for recording, analyzing or displaying human physiological data sources which underlie such behavior.

Linn 4,163,941 shows a system similar to Haas et al. above and is intended for environment in which knowledge of results is important. In this system video information is processed for calculating the velocity of a golf club head. Such data and results can then be analyzed by comparing the relative velocities during different club swings. The limitation of this system thus follows the ways of Haas et al. but a further limitation resides in the fact that the system is restricted to a fixed, single calculation of behavior.

Criglar et al. 4,170,225 describes a biofeedback device which is generally contained within the prior art but is otherwise limited to a single, fixed measure of EMG activity.

Jones et al. 4,250,890 shows a device including a computer and within a system dedicated to measuring the computing respiratory parameters. The computer performs a single calculation, and its function or purpose cannot be controlled; nor its results coordinated, with the actions of other computers or processors.

Cromarty 4,304,406 relating to a golf training and practice apparatus is yet another example of a device which produces a display which is useful for instances requiring knowledge of results. This device includes a television display and plurality of sensors for sensing positions of the head of a golf club during the swing at a ball in a given location. One embodiment includes a single microprocessor and a series of fixed purpose sensors. Interchangeable transducers for detection of physiological signals do not form part of the structure.

Connelly 4,337,049 describes a method and system for automated training of manual skills and in the apparatus involved body motion is measured, compared to a reference motion and an appropriate training signal (which is a function of a motion error value and a proficiency level of the subject) provided to the user. This apparatus carries out a fixed sequence of operations from which it cannot deviate such as those changes which would be necessary if a different sensor was introduced into the system. These operations relate to training manual skills and do not include provision for interchangeable physiological transducers, nor a multiplicity of "tightly coupled" computers for integration, coordination and control of physiological transducers, into a single apparatus, with the biofeedback method adapted to operate with such multiprocessor architectures.

SUMMARY OF THE INVENTION

This invention relates first to a novel method which includes a multiplicity of computers. They are arranged to perform a number of subtasks associated with the acquisition of skilled performance, as might be encountered in a sport or activity such as the improvement of human body condition, tone, or well-being. One of the computers is adapted to coordinate the calculations of control functions carried out by the other computers. The subtasks include: the transduction and acquisition of any of a variety of physiological signals, calculation of a meaningful measure of these electrical analogs, presentation and display (including visual and auditory) of these measures (possibly in the form of a game), comparison of these measures against a criterion which can be simply introduced into one of these computers and which follows an arbitrary function of several parameters including time, and level of performance, and calculation of an error between a desired performance measure and the actual performance measure.

This invention relates, secondly, to a novel method of skill enhancement, or improvement of well-being which may be incorporated or used in combination with devices of this type such that no further human intervention is needed in order to accomplish the desired performance goals other than the user.

OBJECTS OF THE INVENTION

It is among the principal objects of this invention to provide improved means for the introduction of physiological data into a computer or electronic game.

Another object of the invention resides in novel means utilized for improving the speed of operation of physiological data processing devices such that calculations on such data can be made available within times which are meaningful for learning of human behavior and responses.

A further object of this invention lies in an improved method of introducing into computers variable acquisition and display protocols associated with physiological data processing.

Another object of the invention resides in an improved, novel and automatic method of alteration and adaptation of performance of physiological data processing computers in response to the physiological data.

A further object of this invention is to provide a novel method for development of skill enhancement in conjunction with physiological data processing computers.

Yet another object of this invention is to provide an improved and novel method of skill enhancement which requires no human intervention other than the user and which can accomplish such conditioning of human beings in an automatic manner.

Further, the object of this invention is to provide a novel and closed-loop method of learning to carry out repeatedly and appropriately certain behavioral responses, including desired muscular responses. And finally, the object of this invention is to provide a novel and improved method of narrowing during the actual performance and in real-time, the gap between simultaneously displayed actual behavioral response and the desired behavioral goal.

These objects and other incidental ends and advantages of the invention will appear in the progress of the disclosure and as pointed out in the appended claims.

DRAWINGS OF PREFERRED EMBODIMENT

In the accompanying drawings showing a preferred form of the invention:

FIG. 4A and its continuation

DESCRIPTION OF THE PREFERRED EMBODIMENT

Figure 1:
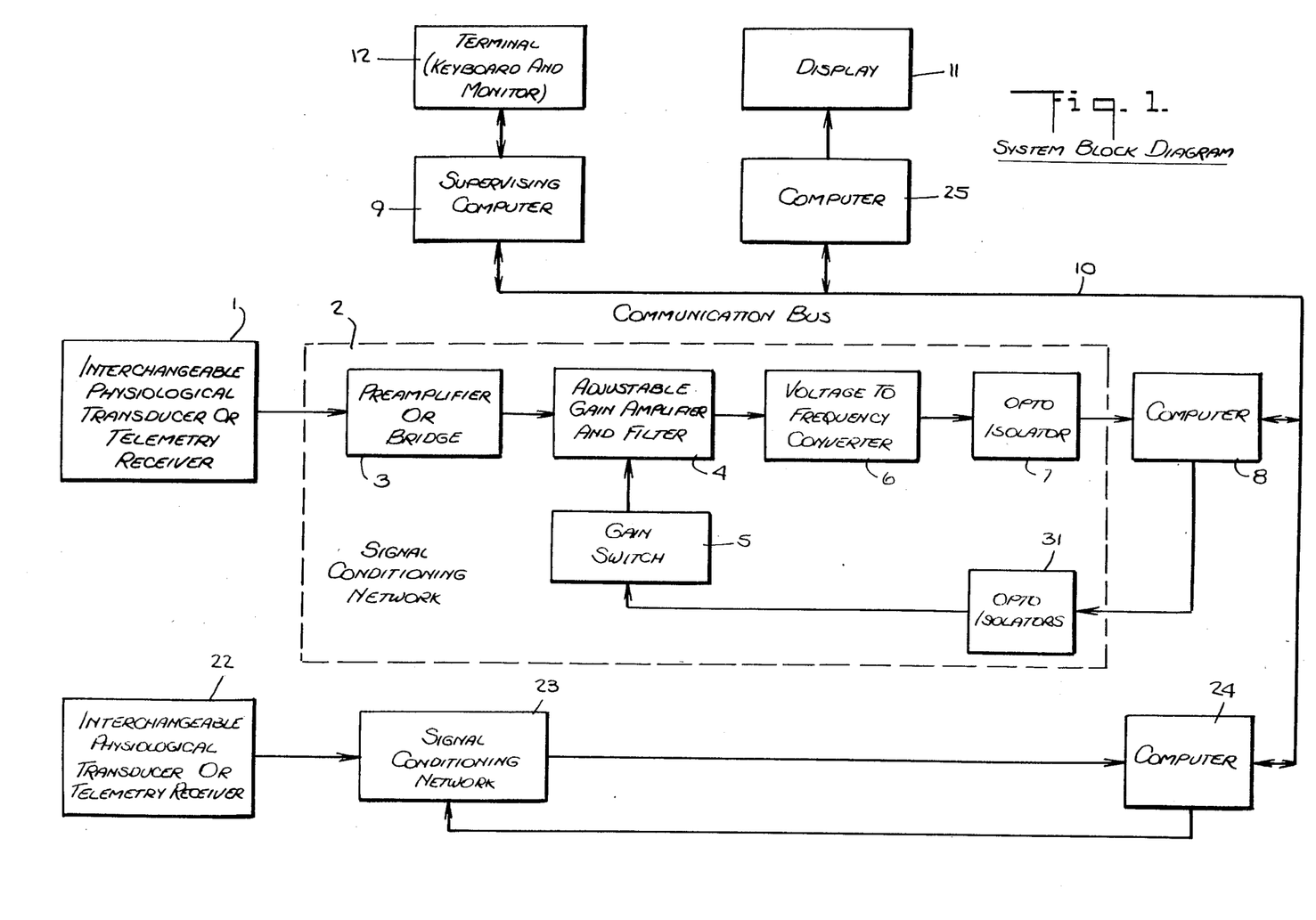
FIG. 1 is a System Block Diagram of the present invention, illustrating the logical and fnnctional relationships between the transducers, signal conditioning networks, and plurality of computers.

FIG. 1

The apparatus of the present invention is shown in the System Block Diagram of FIG. 1. The skill enhancement system is divided into a fixed portion and a system of variable or replaceable elements. The fixed portion is intended to meet all possible physiological and/or behavioral environments and applications. The invention can be adapted, without modification, to industrial or scientific purposes, providing cost effective instrumental solutions to data acquisiton applications in these environments. Binary coded sequences stored in both the fixed and replaceable program memory means found in the present invention provide for control of the system. In addition, signal transducers convert physiological, behavioral, or other sources of information into electrical equivalents. Binary sequences stored within the various memory means control displays such as those which may be found in electronic games, and also control the signal processing that is to be performed on the electrical signals received from the signal transducers.

A number of different transducers can be directly integrated into the system. The following but not exhaustive list indicates a number of transducers which are compatible with the skill enhancement system together with their appropriate physiological source. These transducers form part of the replaceable portion of the skill enhancement system.

| Physiological Function | Transducer |
| --- | --- |
| Muscle (EMG) | Electrodes, piezoelectric |
| Brain Waves (EEG) | Electrodes |
| Heart rate, pulse rate and blood pressure | Photo detection |
| Respiration | Resistance (strain gauge) |
| Temperature | Resistance (thermistor) |
| Position | Resistance (goniometer) |
| Force | Resistance (spring deflection) |
| Galvanic skin resistance | Resistance |

Signals from these transducers may be connected or integrated directly into the system. In addition, transducer signals may be used to modulate a carrier signal. The resultant signal can be transmitted from a remote location to the skill enhancement system where a receiver carries out demodulation. The resultant demodulated information, physiological or other, can be integrated into the present invention.

Any or all of a plurality of interchangeable physiological transducers or telemetry receivers 1 and 22 generate signals or data in correspondence with human electrical activity, changes in body volumes, temperature, or positional changes of limbs or other parts of the human anatomy. These are transmitted to a corresponding plurality of signal conditioning networks as 2 and 23 adapted to receive such signals and to process the data such that it is suitable for transmission to a computer. Signal conditioning network 2 is identical to signal conditioning network 23. In order to carry out such processing, a signal conditioning network 2 or 23 accepts signals from interchangeable physiological transducer or telemetry receiver 1 or 22 and transmits these to preamplifier or bridge 3. If, for example, the interchangeable physiological transducer or telemetry receiver 1 includes resistive transduction, its effect is detected in a standard bridge circuit (in preamplifier or bridge 3) well known to those familiar with the art. If interchangeable physiological transducer or telemetry receiver 1 generates or detects signals which are electrical in nature, such as those of muscle (EMG), brain waves (EEG), heart (EKG), or force (piezoelectric), then such signals are amplified by preamplifier or bridge 3. Outputs of preamplifier or bridge 3 are further amplified in adjustable gain amplifier and filter 4. Gain switch 5 determines the amplification factor or gain associated with adjustable gain amplifier and filter 4. Operation of gain switch 5 will be discussed below; however, the following description of the need for adjustable gain amplifier and filter 4 in the present invention is deemed apposite. When the skill enhancement system is used in applications requiring measurement of heart rate, the amplifier gain will be set to a high value. The reason for this is linked to the transduction mechanism for detection of heart rate. In the example of heart rate detection (as part of a method of behavior modification) an optical source may illuminate a user's finger (or other part of the human anatomy). The user's blood flow which is related to the occurrence of a heart beat modulates the light received at an optical detector located near the source of illumination. This modulated signal eventually appears at signal conditioning network 2. In order to compute heart rate, only the time between beats is important. Consequently, only the time at which a modulation peak occurs is of interest. The amplifier gain of adjustable gain amplifier and filter 4 is set at a high value by the combination of gain switch 5 and computer 8 in order to detect such modulation peaks.

In the example of the measurement of muscle responses in which EMG measurement is appropriate, the gain or amplification factor of adjustable gain amplifier and filter 4 by the combination of computer 8 and gain switch 5 will be adjusted in a different manner. If the amplification is too high, the system will "saturate" and any measures of such EMG activity will go "off scale", especially when a user makes a muscular contraction. The gain must be adjusted so that this does not happen. Thus, the gain setting must be flexible and vary from one user to the next. The gain can be adjusted such that maximum measurements from a given user does not saturate the system. Signals are "normalized" with respect to such a user. Any methodology subsequently employed to modify behavior is made independent of absolute signal level—the system will work for "weak" and "strong" users alike.

The amplified and filtered signals from adjustable gain amplifier and filter 4 are electrical equivalents of physiological data. These are transmitted to voltage to frequency (V/F) converter 6. Within voltage to frequency converter 6 the electrical equivalent of the physiological data are converted to a train of equipotential pulses whose frequency is proportional to such physiological equivalent data. These pulses are transmitted to computer 8 via opto-isolator 7. Opto-isolator 7 is included in order to prevent or minimize electrical shock hazard to a user. Any and all circuits of the skill enhancement system which are in contact with a user are powered by batteries. These circuits have no direct contact with the power mains. The equipotential pulses which are generated by voltage to frequency converter 6 pass through opto-isolator 7 to components which may have contact with the power mains.

The signals reaching computer 8 which forms part of the fixed portion of the skill enhancement system consist of equipotential pulses of variable frequency. Variation of the frequency of such pulse trains is in correspondence with human physiological or other data. The frequency variation contains the information associated with the original sources. Computer 8 contains a plurality of binary sequences. A multiplicity of these sequences are adapted to process the train of variable frequency, equipotential pulses received from opto-isolator 7. The table shown below indicates what processing calculations the multiplicity of binary sequences within computer 8 are adapted to perform, and under what circumstances such calculations would be relevant. Computer 24 performs similar functions or signals received from signal conditioning network 23.

TABLE OF BUILT-IN DATA PROCESSING CALCULATIONS

| Computation | Mathematical Function | Uses |
|---|---|---|
| Count number of pulses per unit time. | Integration | Muscle activity Brain activity |
| Difference between highest and lowest frequencies. | Peak to peak detection | Respiration |
| Time of occurrence of highest frequency. | Peak detection | Heart rate |
| Frequency at any (all) point(s) in time. | Signal magnitude (analog to digital conversion) | Temperature Limb position |

This table is not exhaustive but is representative of the possible uses. The function(s) to be carried out—the particular processing to be performed—is transmitted from supervising computer 8 and will be described subsequently. The processing to be performed, in the form of a command, is transmitted from supervising computer 9 to one or more computers such as computer 8, 24 and/or 25 via communication bus 10. Communication bus 10 contains signals comprised of addresses, data and control. Such busses are well known to those familiar with the art. The equipotential pulses are processed within computer 8 (or 24) and results of such computations are returned or transmitted from one or more computers 8 or 24 to supervising computer 9. Transmission of such results takes place via communication bus 10. Thus, supervising computer 9 transmits commands, and data or parameters to computers 8 and 24 and these latter computers may return or transmit computed data or results to supervising computer 9. Transmission of information on communication bus 10 is under the control of supervising computer 9. The processed information which is returned from computers 8 and/or 24 to supervising computer 9 can subsequently be incorporated into a display or electronic game. This is accomplished by transmission of such computed or processed results from the supervising computer 9 (where it has been received from one or more computers 8 or 24 to yet another computer 25 which contains binary coded sequences within its memory for control of a display 11 or electronic game). These binary coded sequences are adapted to accept such processed data from the supervising computer 9 and to alter or modify the display 11 which may be associated with an electronic game. Such display 11 can be either visual or auditory or tactile, or a combination of being visual, auditory and tactile.

Such a display provides a user with a knowledge of his or her physiological or motor behavior or performance. The combination of interchangeable physiological transducer or telemetry receiver 1 (or 22), signal conditioning network 2 (or 23), plurality of computers 8, 24 and 25, communication bus 10, supervising computer 9, display 11, and terminal 12 (comprising keyboard and monitor and to be described subsequently), can be incorporated into a method of training athletic performance, including sports and fitness. Such a method can be based on comparison of qunatified information reflecting actual and desired and/or optimal activity in key muscles or other parts of the human physiology involved in the production of a particular behavior or skilled performance.

The force and velocity of varying muscular activity can be determined in "real time" (in which results are provided to a subject in time to alter behavior or performance during its evolvement and not inordinately delayed from the time of occurrence of a behavior) by the present invention and displayed for a user. The user can integrate such knowledge of performance during activity and compare results with ideal or desired performance levels which can also be integrated into the display or electronic game. Such ideal and/or optimal performance goals can be based upon or normalized with respect to an individual's present level of performance. Alteration of the user's performance toward a more desirable value of force and velocity of muscular activity is achieved in consecutive trials or behaviors by reducing the gap between the actual and the desired performance as reflected in the display or electronic game. This training procedure takes place in a step-by-step manner, with the user learning the specific control over spatial-temporal activity of key muscles or other parts of the human anatomy or physiology until coordinated control is achieved and patterning or an automatic, dynamic, skilled behvior or movement is established. At this stage there is no further need for the cognitive information provided during training by the closed loop interaction specific to the described method.

In order to provide control of the entire method or sequence of operation, the user may communicate intentions such as "begin operation" via terminal 12 which is connected to supervising computer 9. Terminal 12 comprises a keyboard and monitor or television receiver and is well known to those familiar with the art. Supervising computer 9 receives binary sequences which are coded representations of alphanumeric characters from the keyboard of terminal 12 and transmits binary coded sequences representative of alphanumeric characters to the monitor associated with terminal 12.

Figure 2:
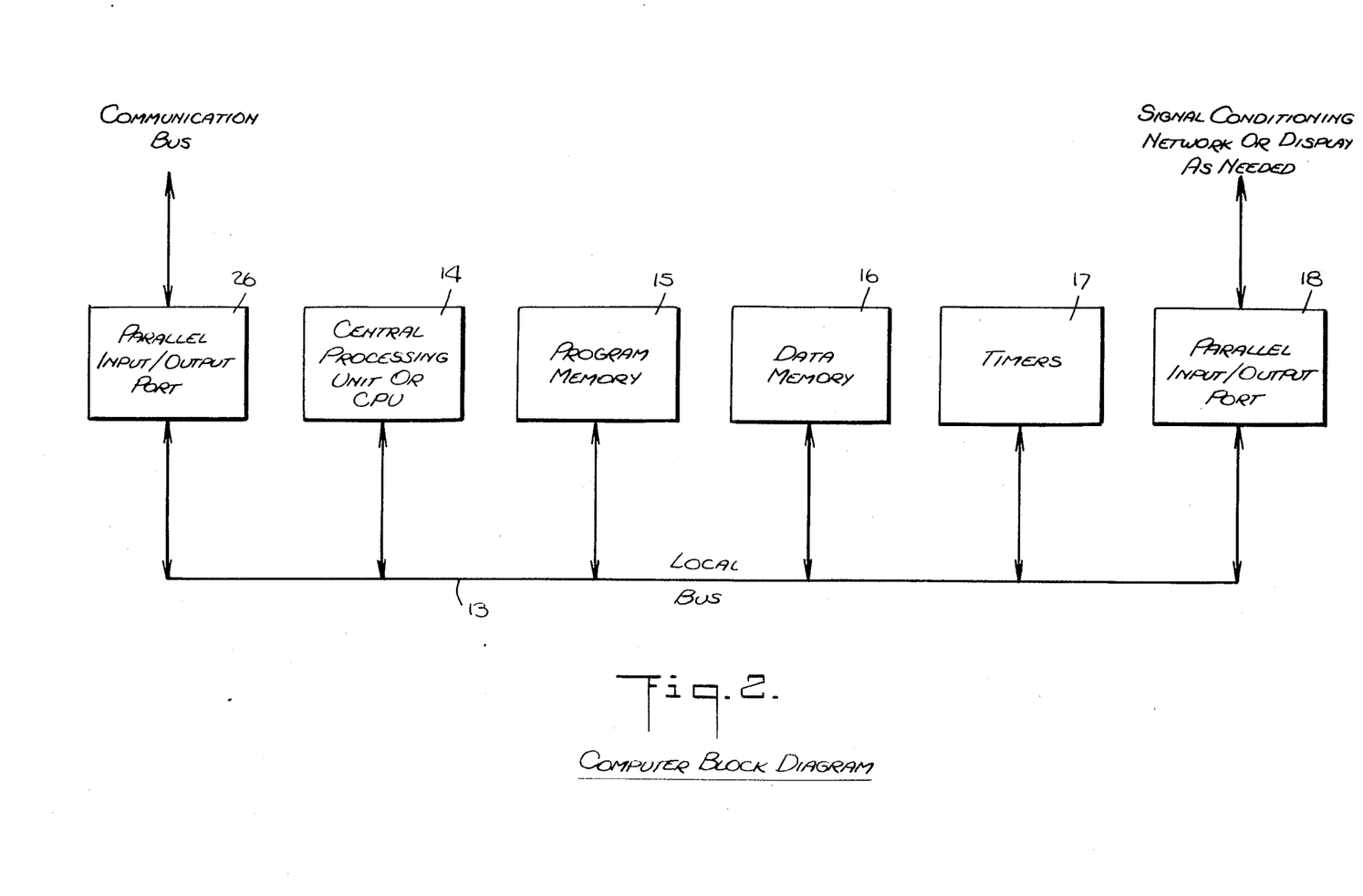
FIG. 2 is a Computer Block Diagram of the computers which control the signal conditioning networks and/or display devices of the present invention and showing logical elements to communicate with the supervising computer and to control the signal conditioning networks and/or display.

FIG. 2

FIG. 2 is a Block Diagram of computers 8, 24 or 25 indicating the logical and functional elements needed to carry out the processing of data required by the present invention. Within computers 8, 24 or 25 communication between various elements takes place via local bus 13. Local bus 13 comprises address lines for identification of the element sources and destinations of data within computers 8, 24 or 25. In addition, local bus 13 includes data lines or signals which contain the information to be transmitted between elements of computers 8, 24 or 25. Finally, local bus 13 includes control lines which determine the time and manner in which data is transmitted between elements of computer 8, 24 or 25. Local bus 13 is of a type well known to those familiar with the art. Central processing unit (or CPU) 14 carries out the following operations: interpretation of the instruction to be performed by computer 8, 24 or 25; arithmetic calculations on the data processed by computer 8, 24 or 25; and logical comparisons and operations on the data processed by computer 8, 24 or 25. Program memory means 15 contains a plurality of binary sequences whose coded form defines the operations to be performed by computer 8, 24 or 25. Each of the plurality of computers 8, 24 or 25 in the present invention may contain a distinct and separate plurality of such binary sequences. Data memory 16 stores data as from opto-isolator 7, results of computations within computers 8, 24 or 25, and partial results of computations or logical operations within computers 8, 24 or 25. Computers 8, 24 and 25 also each contain a multiplicity of timers 17. These timers are controlled by the combination of central processing unit 14, program memory 15, and local bus 13. Such timers keep track of the times at which events are to occur such as those times at which data from opto-isolator 7 are to be processed (such data being representative and in correspondence with physiological or other information) or the length of time that a sound or visual presentation is to remain on the display 11 or electronic game associated with the present invention. Finally, each of computers 8, 24 and 25 contains a plurality of parallel input/output ports such as 18 and 26. Such ports consist of registers or one-celled memory locations adapted to receive or transmit binary information. Such information may be received or transmitted to communication bus 10. In addition, such ports can be used to transmit or receive data from a signal conditioning network 2 or 23 or display 11. The plurality of computers 8, 24 and 25 may be similar to the 8048, 8049 or 8051 microcomputers manufactured by the Intel Corp., or they may be similar to other microcomputers which are commercially available.

Figure 3:
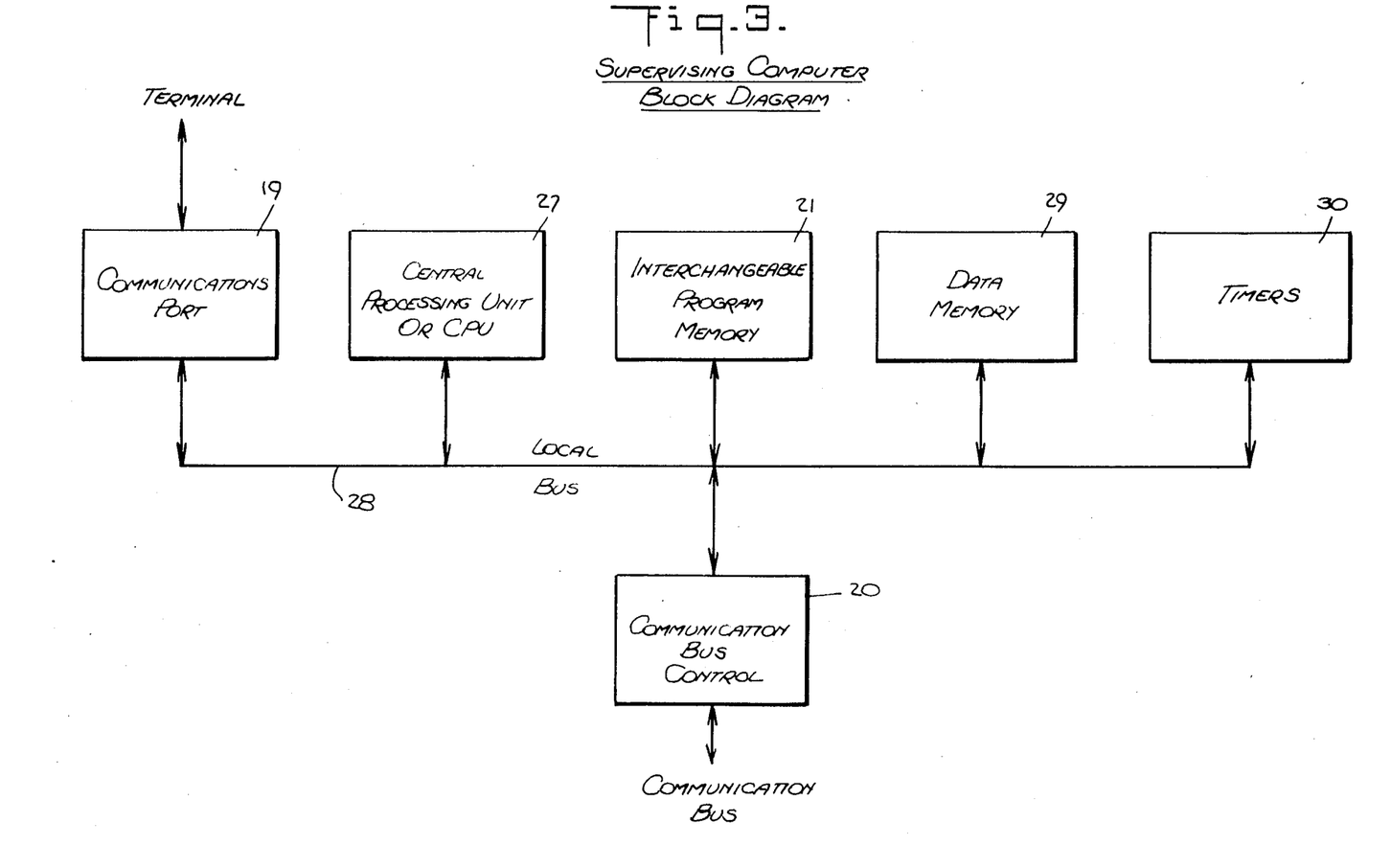
FIG. 3 is a Supervising Computer Block Diagram of the supervising computer of the present invention showing logical elements needed to interact with a human user and control other computers in the system.

FIG. 3

Supervising computer 9 is shown in the Supervising Computer Block Diagram of FIG. 3. Communication between elements within supervising computer 9 takes place via local bus 28. In a manner analogous to the structure of computers 8, 24 and 25, supervising computer 9 contains: a central processing unit 27, a data memory 29, and a plurality of timers 30. Supervising computer 9 contains communications port 19 which is adapted to transmit and receive data from terminal 12, such transmissions taking place in a data serial manner. Communication bus control 20 is adapted to transmit or receive data from the plurality of computers 8, 24 and 25. Supervising computer 9 contains one of the interchangeable parts of the present invention in the form of interchangeable program memory 21. Interchangeable program memory 21 contains yet another plurality of binary coded sequences. This latter plurality of binary coded sequences contains data and instructions to be carried out or executed by central processing unit 27 of supervising computer 9. Such binary coded sequences define the operations, processing or calculations to be carried out by the plurality of computers 8, 24 and 25. Such data and instructions may include (but are not limited to) information regarding gain settings of adjustable gain amplifier and filter 4 to be selected via gain switch 5, the calculation to be performed by other or both of the computers 8 and 24 such as the peak frequency of the pulse train transmitted from one of the opto-isolators 7 to one of the computers 8 or 24, or to control the visual or auditory display which appears on display 11 via computer 25, such display being integrated into an electronic game adapted to support the skill enhancement method of this present invention. Supervising computer 9 may be like any of a number of computers which are commercially available not excluding the TI-99/4A manufactured by Texas Instruments Inc.

Figure 4A:
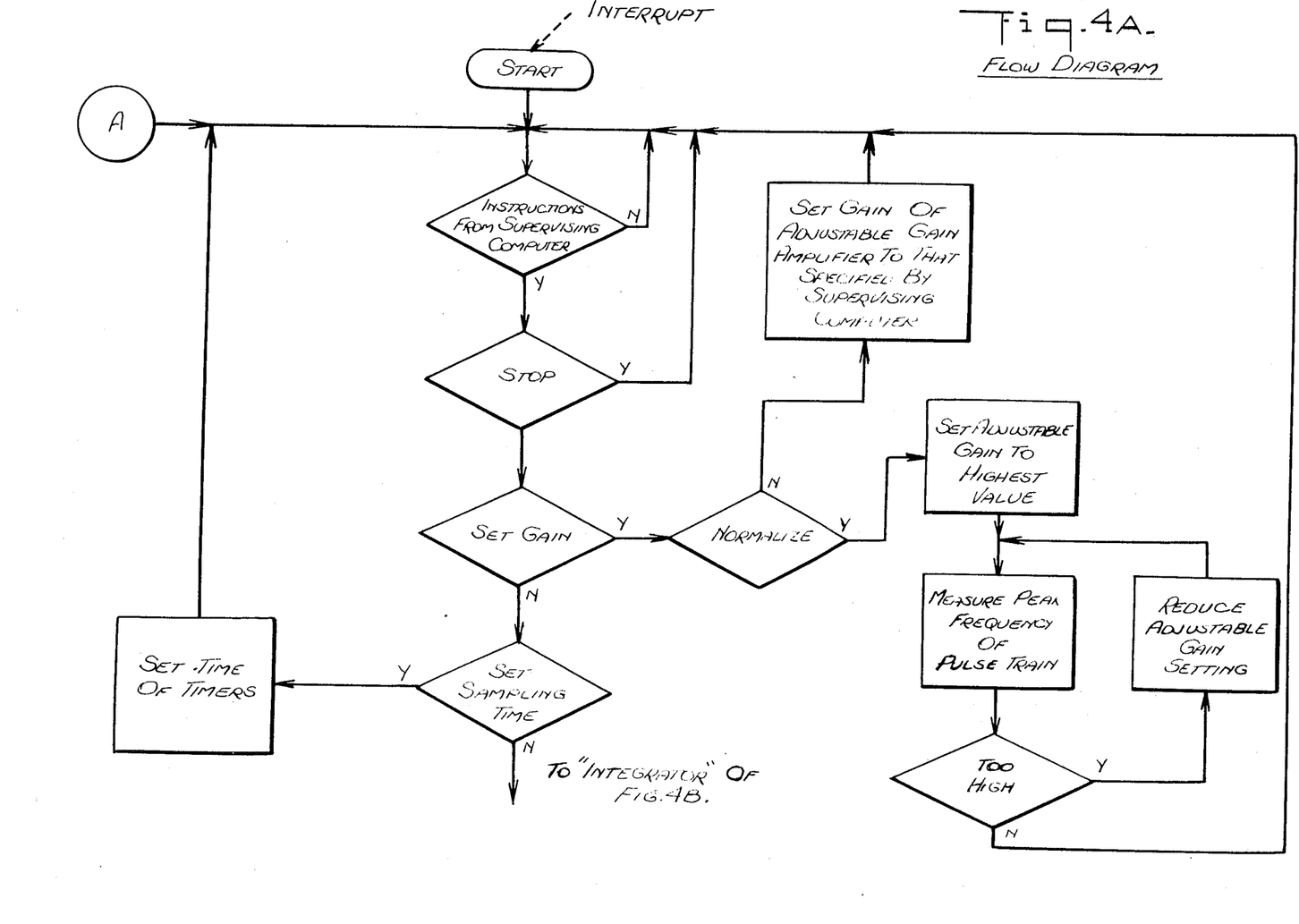
Figure 4B:
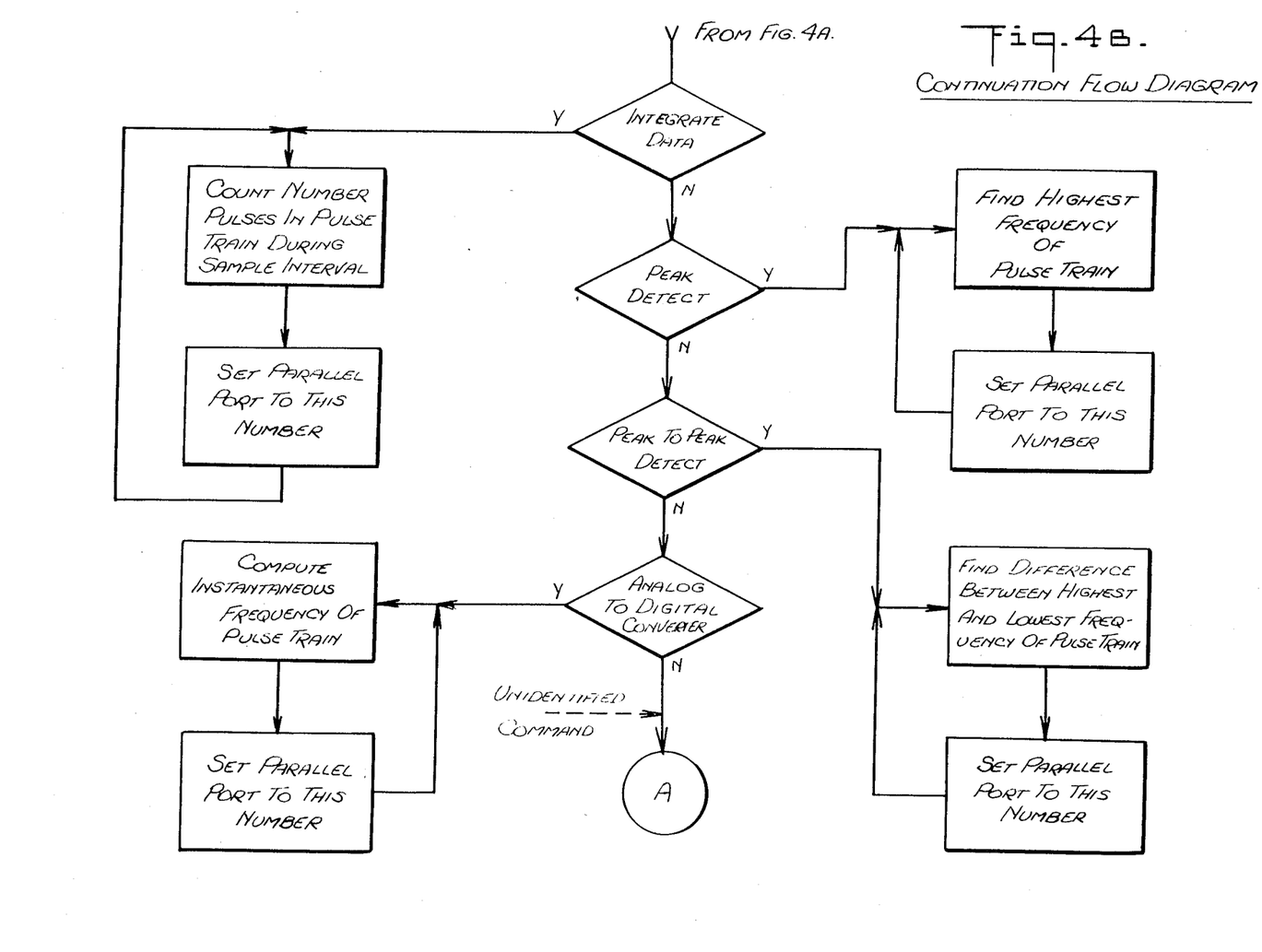
FIG. 4B is a Flow Diagram showing the operations which the plurality of computers 8, 24 and/or 25 may be adapted to perform on data received from the plurality of signal conditioning networks 2 and 23.

FIGS. 4A–4B

FIG. 4A and continuation 4B is a Flow Diagram describing the operations which either or both of the computers 8 or 24 may be adapted to perform. Computers of the type which are used for any or all of the plurality of computers 8, 24 and 25 such as the Intel 8048 are reset upon application of electrical power. In the case of the Flow Diagram of FIGS. 4A and continuation 4B, such an event will cause the sequence of operations to begin at the symbol marked START. From that point in time (or in the Flow Diagram) the precise sequence of operations to be performed can be understood by following the arrows of FIG. 4. Where a decision path is encountered, the actual sequence to be followed depends on the assumed result of such a decision (Y for yes or true, N for no or false). In addition to the reset upon application of power to any or all of the computers 8, 24 or 25, the supervising computer 9 may send a signal to any or all of the computers 8, 24 or 25 in order to reset these computers or to initiate operation at the START.

As indicated in the Flow Diagram of FIG. 4, either or both computers 8 or 24 sit in a loop or idle state until instructions are received from superivising computer 9. Upon receipt of an instruction or command, the computer 8 or 24 enters a "skip chain." In such a chain, a series of decision paths is followed in order to determine which instruction has been transmitted from the supervising computer 9 to the computer 8 or 24. The commands which are possible include but are not limited to: stop, set gain, set sampling time, perform integration of the data (INTEGRATE DATA), detect data peak, detect peak to peak excursion of the data, or perform analog to digital conversion. The operations performed during these command sequences are as follows:

(1) Stop command.

If the command is a stop command, either or both of the computers 8 or 24 will cease any operations in progress and return to a sequence which simply awaits further instructions from supervising computer 9.

(2) Set gain command.

If either or both of the computers 8 or 24 receives a set gain command then the gain of the adjustable gain amplifier and filter 4 of either signal conditioning network 2 or corresponding signal conditioning network 23 will be set when this command is fully executed. The set gain command from supervising computer 9 could include a parameter which specifies whether the gain is to be set to an absolute value or if the gain is to be normalized in accordance with the physiological or other data received by computer 8 or 24 from signal conditioning network 2 or 23. If the gain is to be set to an absolute value then computer 8 or 24 sets a number into parallel input/output port 18. This number is transmitted via opto-isolator 31 to gain switch 5. Gain switch 5 selects the amplification factor associated with adjustable gain amplifier and filter 4. When this is complete, computer 8 or 24 awaits further commands from supervising computer 9. If, however, the set gain command is accompanied by a parameter which indicates that a normalized gain is to be established, then a different procedure is followed. In such circumstances computer 8 or 24 starts by setting the amplification factor of adjustable gain amplifier and filter 4 to its maximum value. Setting such a gain factor is accomplished as before—a number is deposited in parallel input/output port 18 followed by transmission of this number to gain switch 5 via opto-isolators 31. Computer 8 or 24 now computes the peak frequency of the pulse train received from voltage to frequency converter 6 via opto-isolator 7. If this exceeds a maximum value, then the gain of adjustable gain amplifier and filter 4 is reduced and the frequency of the pulse train again tested. The process of sampling the pulse train and adjusting the amplification factor continues until such time as the peak frequency of the pulse train falls below an appropriate value. Computer 8 or 24 has now completed the normalized adjustment of the gain and again awaits the transmission of further commands.

(3) Set sampling time command.

If the computer 8 or 24 has received a command to set the sampling interval timing, then the number corresponding to such a sampling interval is transmitted to the timers 17 of computer 8 or corresponding timers of computer 24. This time determines the points at which data from the signal conditioning netowrk 2 or 23 is examined.

(4) Integrate data command.

If computer 8 or 24 has received a command to perform mathematical integration of the data which is received from signal conditioning network 2 or 23, then such computation is initiated. Numerical integration of the data transmitted from signal conditioning network 2 or 23 is achieved by summation of the number of pulses per unit of sampling interval. This computed number is stored in parallel input/output port 18 where it may be read by supervising computer 9. Such integration continues until a stop or other command is received by computer 8 or 24 from supervising computer 9.

(5) Peak detect.

If computer 8 or 24 has received the command to compute the peak value of the data associated with the physiological data, then this is achieved by computing the highest frequency of the pulse train received by computer 8 or 24 from signal conditioning network 2 or 23. As the frequency of the pulse train is proportional to the physiological or other data received by the present invention, then the highest frequency of the pulse train will correspond to the peak magnitude of the original data. In order to prevent a local peak from determining this value for all time, the peak value represents that value during each of the sampling intervals as determined by timer 17. This value is transmitted to parallel input/output port 18 where it can be read by supervising computer 9. Computation of the peak value during each sampling interval continues until supervising computer 9 transmits a new command.

(6) Peak to peak detection.

Supervising computer 9 may transmit a command to compute the total excursion of the physiological or other data received by the present invention. Such calculation is performed by computing the difference between the largest and smallest value of the frequency of the pulse train received by computer 8 or 24. As the frequency of the pulse train is proportional to the physiological or other data received by the present invention, the excursion (peak to peak value or magnitude) of such data can be found by computing the difference between the highest and lowest frequency of the pulse train. This calculation is performed during the sampling interval as specified by timers 17. For each sampling interval the result is transmitted to parallel input/output port 18 where it can be read by supervising computer 9. Peak to peak calculations once initiated continue indefinitely until a new command is received by computer 8 or 24.

(7) Analog to digital conversion.

If the command received by computer 8 or 24 is to convert the physiological or other data into a numerical quantity, then the frequency of the pulse train received by computer 8 or 24 from signal conditioning network 2 or 23 is converted into an equivalent number at times determined by the sampling interval determined by timer 17. This number, proportional to the frequency of the pulse train, is also proportional to the physiological or other data. This number is deposited into parallel input/output 18 where it may be read by supervising computer 9. Analog to digital conversion continues until computer 8 or 24 receives a new command.

Should computer 8 or 24 fail to identify the signals received from supervising computer 9 as a legitimate command, then such signals are ignored and the computer 8 or 24 resumes an idle state awaiting further commands or instructions from supervising computer 9.

APPLICATIONS OF INVENTION

The following discussion will illustrate one way in which the present invention may be employed to enhance physical fitness and well-being. Isometric exercise has long been considered to be beneficial to human well-being. In such exercise a user employs muscular contraction occurring when the ends of the muscles are fixed in place so that significant increases in tension occur without appreciable change in muscle length. To perform such exercises in a beneficial manner a protocol must be followed so as not to overly stress the user. Thus, the applied force must be within defined limits, neither too much force nor too little force. In the case of the present invention the force being applied by the user is detected in the manner heretofore described in one of the plurality of computers 8 or 24. This force as a function of time is transmitted to the supervising computer 9. The supervising computer contains a binary coded sequence which has been stored within interchangeable program memory 21 which compares such computed force measurement against acceptable limits. Information regarding the error between the desired force and the actual force is transmitted to computer 25 which contains a binary sequence which controls display of this information. Such display can form the basis of a game. In one such example, a graphic image of a car appears on a television screen. The width of the roadway and a series of obstacles (such as steep hills or other cars on the road) also appearing, the visual display is modulated or varied in accordance with the error information received from supervising computer 9. The closer the user keeps to the desired protocol, the higher the score associated with the electronic game. User performance may also be reflected in changes of the width of the highway image and the occurrence and number of obstacles. The computer 25, which controls the visual display, can also be made to provide auditory information such as the sound of a crash if the user's performances cause the target vehicle on the display to strike one of the obstacles such as another car.

CONCLUSION

Thus, there has been shown and described in addition to the novel device, a novel method for integration of physiological signals into one or more of a plurality of computers, and display of measurements made upon such signals to provide on-line, real-time feedback of such physiological signals to an observer.

It is understood that minor changes, modifications and variations of described structure, systems and method as well as other uses and applications of the subject invention may all be resorted to without departing from the spirit of the invention and the scope of the appended claims.

We claim:

1. A training device for selectively monitoring one or more of a plurality of physiological signals produced by a human being and for displaying computed measures of such signals including:
   (a) a plurality of replaceable, selectable and interchangeable transducer means adapted to be singly and plurally utilized for conversion of said plurality of physiological signals into a corresponding plurality of equivalent electrical signals;
   (b) a plurality of corresponding signal conditioning means for said equivalent electrical signals including adjustable electrical amplification means, filtering means and conversion means adapted to convert said plurality of said conditioned equivalent electrical signals into a corresponding plurality of equivalent equipotential pulse trains, each of whose instantaneous frequencies is proportional to each of said corresponding plurality of said conditioned equivalent electrical signals;
   (c) a plurality of display means operative for presentation of said plurality of equivalent equipotential pulse trains as computed measures of said physiological signals;
   (d) terminal means for control of said training device by the said human being;
   (e) a plurality of relatively independent computer means cooperating in selective combinations and at least one combination of which is adapted to calculate said computed measures of said corresponding plurality of equivalent equipotential pulse trains, and another combination of which is adapted to control at least one of said plurality of display means;
   (f) supervising computer means adapted to control, select and/or coordinate said plurality of said relatively independent computer means; and
   (g) communication bus means adapted to transmit information between said plurality of relatively independent computer means and said supervising computer means.

2. A training device as in claim 1 wherein said plurality of display means each includes at least one of:
   (a) visual display means for the presentation of visual stimuli or pictures, and
   (b) auditory display means for the presentation of audible stimuli or sounds to said human being.

3. A training device as in claim 1 wherein said plurality of replaceable, selectable and interchangeable transducer means each includes at least one of:
   (a) electrode means adapted to conduct electrical activity produced by said human being to said device;
   (b) photo detection means and a light source in optical proximity to said photo detection means wherein light from said light source is modulated by physiological signals such as blood flow before reaching said photo detection means wherein electrical activity is produced in correspondence with said modulation and coupled to said device;
   (c) variable resistance means such that variation of human limb or body volume or position causes corresponding variation in resistance of said resistance means which is coupled to said device;
   (d) piezoelectric means adapted to generate electrical charge in correspondence with variation of force or pressure upon said piezoelectric means by physiological signals such as activity of human muscle which is coupled to said device.

4. A training device as in claim 1 wherein:
   (a) a plurality of transmitters are provided corresponding with said plurality of replaceable, selectable and interchangeable transducer means, said plurality of replaceable, selectable and interchangeable transducer means being adapted to modulate a corresponding plurality of electrical carrier signals with information equivalent to said physiological signals; and
   (b) wherein a plurality of corresponding remote receiver means are provided to which said information is transmitted; and
   (c) wherein said information is demodulated and coupled to said signal conditioning means.

5. A training device as in claim 1 wherein each of said plurality of signal conditioning means further comprises:
   (a) preamplifier means adapted to amplify electrical signals received from any one or more of said plurality of replaceable, selectable and interchangeable transducer means such that physiological information is contained in the instantaneous variation of the magnitude of said electrical signals;
   (b) adjustable gain amplifier and filter means including adjustable electrical amplification factor means adapted to further amplify electrical signals received from said preamplifier means;
   (c) gain switch means adapted to vary the said adjustable electrical amplification factor of said adjustable gain amplifier and filter means;
   (d) voltage to frequency converter means adapted to receive electrical signals from said adjustable gain amplifier and filter means and to generate an equipotential pulse train wherein the instantaneous frequency of said pulse train is in correspondence to the instantaneous variation of the magnitude of said electrical signals;
   (e) photo detector means and opto-isolator means including a first light source which is in close proximity thereto, said opto-isolator means being adapted to convert said equipotential pulse train into a corresponding and second equipotential pulse train; and (f) a second and plurality of photo detector means and a plurality of second opto-isolator means including a second plurality of light source means and in close proximity to said second plurality of photo detector means, said second equipotential pulse train being transmitted to at least one of said plurality of relatively independent computer means and being adapted to receive pulses from said plurality of relatively independent computers and to transit said pulses to said gain switch.

6. A training device as in claim 1 wherein each of said plurality of relatively independent computer means further comprises:

(a) central processing means wherein arithmetic operations, comparison of numbers, logical operations, and interpretation and execution of instructions are performed;

(b) program memory means containing a plurality of binary sequences adapted to contain control sequences from said central processing means;

(c) data memory means adapted to contain a second plurality of binary sequences including: results of arithmetic and logical operations performed in said central processing means, a summation of said equipotential pulse trains from said signal conditioning means, control sequences from said supervising computer means, and parameter sequences from said supervising computer means;

(d) a plurality of timer means adapted to accept a third plurality of binary sequences from said central processing means and to produce a fourth binary sequence after a time determined by said third plurality of binary sequences;

(e) a plurality of parallel input/output means adapted to connect each of said plurality of relatively independent computer means to said communication bus means, and additionally adapted to couple each of said plurality of relatively independent computer means to either said signal conditioning means or to each of said plurality of display means; and (f) local bus means adapted to transit information between said plurality of parallel input/output means, said central processing means, said program memory means, said data memory means, and said plurality of timer means.

7. A training device as in claim 6 wherein the first mentioned of said plurality of binary sequences in said program memory means further comprises:

(a) integration binary sequence means adapted to control said central processing means, said data memory means, said plurality of timer means, and said plurality of parallel input/output means such that the number of said equipotential pulses per unit of time can be transmitted to said plurality of parallel input/output means and to said data memory means, such unit of time being controlled by said fourth binary sequence;

(b) peak binary sequence means adapted to control said central processing means, said data memory means, said plurality of timer means, and said plurality of parallel input/output means such that the maximum frequency of said equipotential pulse train in a unit of time can be transmitted to said plurality of parallel input-output means and to said data memory means, such unit of time being controlled by said fourth binary sequence;

(c) peak to peak binary sequence means adapted to control said central processing means, said data memory means, said plurality of timer means, and said plurality of parallel input/output means such that the difference between the maximum frequency and the minimum frequency of said equipotential pulse train in a unit of time can be transmitted to said plurality of parallel input/output means and to said data memory means, such unit of time being controlled by said fourth binary sequence;

(d) analog conversion sequence means adapted to control said central processing means, said data memory means, said plurality of timer means, and said plurality of parallel input/output means such that the frequency of said equipotential pulse train can be transmitted to said plurality of parallel input/output means and to said data memory means, such transmission being determined at the time controlled by said fourth binary sequence;

(e) normalizing binary sequence means adapted to control said central processing means, said data memory means, said plurality of timer means, and said plurality of parallel input/output means such that said gain switch means is adapted to sequence said electrical amplification factor of said adjustable gain amplifier and filter means from highest value to such value as produces a predetermined frequency of said equipotential pulse train, such predetermined frequency being proportional to the maximum allowed voltage which can be generated by said adjustable gain amplifier and filter means which is consistent with said replaceable, selectable and interchangeable transducer means;

(f) binary visual display sequence means adapted to control said central processing means, said data memory means, said plurality of timer means, and said plurality of parallel input/output means such that a visual presentation or picture appears on said visual display means; and (g) binary auditory display sequence means adapted to control said central processing means, said data memory means, said plurality of timer means, and said plurality of parallel input/output means such that an audible presentation, stimulus or sound issues from said auditory display means.

8. A training device as in claim 1 wherein said supervising computer means further comprises:

(a) second central processing means wherein arithmetic operations, comparison of numbers, logical operations, and interpretation and execution of instructions are performed;

(b) interchangeable program memory means containing a fifth plurality of binary sequences adapted to control said second central processing means, said interchangeable program memory means being capable of being removed from said supervising computer means and replaced with at least one of a plurality of a second interchangeable program memory means containing a sixth plurality of binary sequences adapted to control said second central processing means;

(c) second data memory means adapted to contain a seventh plurality of binary sequences including results of arithmetic and logical operations performed in said second mentioned central processing means, results of computations executed in each of said plurality of computer means, and information transmitted from said terminal means;

(d) second plurality of timer means adapted to receive an eighth plurality of binary sequences from said second central processing means and to generate a ninth binary sequence after a period of time determined by said eighth plurality of binary sequences;

(e) communications port means adapted to receive information from said terminal means and to transmit information to said terminal means;

(f) communication bus control means adapted to receive information from said communications bus means and to transmit information to said communications bus means;

(g) second local bus means adapted to transmit information between said second central processing means, said second data memory means, said second plurality of timer means, said communications port means, and said communication bus control means.

9. A training device as in claim 8 wherein said interchangeable program memory means contains at least one of a tenth plurality of binary sequences and:

(a) adapted to control said second central processing means, said second data memory means, said second plurality of timer means, said communications port means and said communication bus control means such that an eleventh plurality of binary sequences is transmitted to said plurality of relatively independent computer means creating at least one of a plurality of visual or auditory presentations on at least one of the said plurality of display means, or (b) adapted to control said second central processing means, said second data memory means, said second plurality of timer means, said communications port means, and said bus control means such that said information transitted from said plurality of relatively independent computer means can be compared to a selected or computed range of values and such that an error signal proportional to the difference between said information and said selected or computed range is calculated, such error being retransmitted to said plurality of relatively independent computer means, wherein it modifies or alters at least one of said plurality of display means.

10. A method of improving skilled behavior or performance by and for a human being comprising the steps of:

(a) receiving his or her plurality of signals as physiological information at successive instants of time regarding behavior or performance from one or more of a plurality of replaceable, selectable and interchangeable transducer means;

(b) quantifying said physiological information underlying such behavior or performance at said successive instants of time by means of at least one of a plurality of relatively independent and cooperating computer means each having a plurality of discrete functions and adapted to perform at least one of a plurality of discrete mathematical calculations at said successive instants of time and whose results provide a measure of at least one specific aspect of physiological behavior or performance at each of said successive instants of time;

(c) comparing said measured physiological behavioral information at each of said successive instants of time against a predetermined measure for said each of successive instants of time considered to be optimal for said one specific aspect of physiological behavior or performance and calculating by means of a supervising computer means an error quantity for said each of successive instants of time, such error quantity being the difference between the said predetermined measure and said measure of said one specific aspect of physiological behavior or performance of said each of successive instants of time; and (d) displaying by means of at least one of a plurality of selective display means either the said predetermined measure considered to be optimal of said one specific aspect of physiological behavior or performance, or the said error quantity, said one of a plurality of selective display means showing or reflecting at least one of said predetermined measures of said specific one aspect of physiological behavior or performance or said error quantity, said plurality of selective display means being controlled by at least one of said relatively independent and cooperating computer means, said relatively independent and cooperating computer means being adapted to modify any one of said plurality of selective display means.

11. The method defined in claim 10 further including:

(a) utilization of said plurality of selective display means by said human being and affording an opportunity for improvement of skilled performance or behavior, (b) including the steps of progressive modification of performance or behavior by him or her with subsequent reduction of said error quantity.

12. The method defined in claim 10 wherein step (a) thereof includes at least one of the steps of receiving information regarding the position of limbs or other parts of the human body, or receiving a plurality of myographic, encephalic, or cardiographic or hemodynamic information either singly or in any combination thereof, and wherein:

step (b) thereof includes at least one of the steps of calculating the integral of such behavior or performance as a function of time, or the calculation of the peak magnitude or variation of such behavior or performance per unit of time as a function of time, or the calculation of the excursion or peak to peak variation of such behavior or performance per unit of time as a function of time, or the calculation of the instantaneous variation or magnitude of such behavior or performance as a function of time, and wherein:

step (c) thereof further includes the step of calculating a second error which assumes one of two values, taking a first value when the absolute value of the difference between the said calculated measure and the said predetermined measure is in excess of a predetermined lower bound and taking a second value when the absolute value of the difference between the said calculated measure and the said predetermined measure is smaller than said predetermined lower bound, said predetermined lower bound being a predetermined function of both the absolute value of the difference between the said calculated measure and the said predetermined measure and time, and wherein:

step (d) thereof includes at least one of the steps of representation of such information on a television receiver or the like, such representation being in the form of a picture familiar to human beings such that variables associated with said picture are proportional to either said calculated measure of behavior or performance, or said first mentioned error or said second error either individually or in combination, or representation of such information on a speaker or the like, such representation being in the form of sounds familiar to human beings such that variables associated with such sounds are proportional to either the said calculated measure of such behavior or performance, said first mentioned error or said second error, or the said predetermined measure of such behavior or performance either individually or in combination.

13. A method of improving physical fitness or well-being of a human being comprising the steps of:
(a) receiving his or her physiological information regarding behavior or performance or well-being from a plurality of replaceable, selectable and interchangeable transducers;
(b) quantifying said physiological information underlying such behavior or performance or well-being by means of at least one of a plurality of relatively independent cooperating computers adapted to perform at least one of a plurality of discrete mathematical calculations whose results provide a measure of at least one specific aspect of physiological behavior or performance or well-being;
(c) quantifying a predetermined measure based upon said received and quantified physiological information considered to be optimal as a function of said physiological information and time for the specific aspect of physiological behavior or performance or well-being representative of the source of such physiological information by means of supervising computer means;
(d) receiving his or her successive physiological information regarding their respective continued state of behavior or performance or well-being as a function of time from said plurality of replaceable, selectable and interchangeable transducers;
(e) quantifying said successive physiological information underlying such behavior or performance or well-being;
(f) comparing the quantified information from said successive physiological information against said predetermined measure considered to be optimal and calculating by means of at least one of said plurality of relatively independent cooperating computers an error quantity, such error quantity being the difference between said predetermined measure and said quantified measure of said successive physiological information at each successive instant of time, and
(g) displaying either said predetermined measure considered to be optimal, said quantified measure of said successive physiological information, or said calculated error quantity by means of at least one selective display means, as a function of time either individually or in any combination.

14. The method defined in claim 13 wherein:
steps (a) and (d) thereof include at least one of the steps of receiving at least one of a plurality of galvanic, myographic, encephalic, cardiographic and hemodynamic information from said human being; and wherein
steps (b) and (e) thereof include at lease one of the steps of calculation of the integral of said physiological information or said successive physiological information, or calculation of the peak magnitude or variation of said physiological information or said successive physiological information, per unit of time as a function of time, or calculation of the excursion or peak to peak variation of said physiological information on said successive physiological information, per unit of time as a function of time, or calculation of the excursion or peak to peak variation of said physiological information or said successive physiological information per unit of time as a function of time by means of at least one of said plurality of relatively independent cooperating computer means; and wherein
step (f) thereof includes at least one of the steps of calculation of an error quantity consisting of the difference between said successive physiological information and said predetermined measure considered to be optimal, or calculation of an error quantity which assumes one of two values, a first value when the absolute value of the difference between said successive physiological information and said predetermined measure considered to be optimal exceeds a predetermined value, and a second value when said absolute value of said difference does not exceed said predetermined value by means of said supervising computer means; and wherein:
step (g) thereof includes the step of representation of at least one selective display means on a television receiver or the like being in the form of a picture familiar to human beings such that variables associated with said picture are proportional to either said successive physiological information, said predetermined value considered to be optimal, or said error, or representation of said one selective display means on a speaker or the like, being in the form of sounds familiar to human beings such that variables associated with said sounds are proportional to either said successive physiological information, said predetermined value considered to be optimal, or said error by means of at least one of said relatively independent cooperating computer means.

* * * * *